United States Patent [19]
Kirchner et al.

[11] Patent Number: 5,135,002
[45] Date of Patent: Aug. 4, 1992

[54] PRESSURE TRANSDUCER COMPENSATION SYSTEM

[75] Inventors: Richard A. Kirchner, Santa Clara; Timothy A. Shotter, Sunnyvale, both of Calif.; Robert W. Beard, deceased, late of Placerville, Calif., by Wanda S. Beard, Legal Representative/Heir

[73] Assignee: Abbott Laboratories, Abbott Park, Ill.

[21] Appl. No.: 400,274

[22] Filed: Aug. 29, 1989

[51] Int. Cl.[5] .......................... A61B 5/00; G01L 27/00
[52] U.S. Cl. .................................. 128/672; 73/400 R; 73/708; 73/766; 128/673; 364/558; 364/571.03
[58] Field of Search ............... 128/672, 673, 675, 748; 73/1 R, 4 R, 708, 766; 604/65, 67; 338/314; 364/558, 571.03

[56] References Cited

U.S. PATENT DOCUMENTS

| | | | |
|---|---|---|---|
| 4,465,075 | 5/1982 | Swartz | 128/672 |
| 4,501,531 | 2/1985 | Bilstad et al. | 604/67 |
| 4,550,611 | 11/1985 | Czarnocki | 73/718 |
| 4,557,269 | 12/1985 | Reynolds et al. | 128/675 |
| 4,581,940 | 4/1986 | Merrick et al. | 73/708 |
| 4,659,235 | 4/1987 | Gilmore, Jr. et al. | 73/727 |
| 4,679,567 | 7/1987 | Hanlon et al. | 128/675 |
| 4,683,894 | 8/1987 | Kodama et al. | 128/675 |
| 4,685,469 | 8/1987 | Keller | 128/675 |
| 4,817,022 | 3/1989 | Jornod et al. | 73/4 R |
| 4,883,992 | 11/1989 | Koglin et al. | 73/708 |
| 4,926,674 | 5/1990 | Fossum et al. | 73/4 R |
| 4,950,235 | 8/1990 | Slate et al. | 604/67 |

Primary Examiner—Kyle L. Howell
Assistant Examiner—Krista M. Pfaffle
Attorney, Agent, or Firm—Christensen, O'Connor, Johnson & Kindness

[57] ABSTRACT

A pressure transducer compensation system for compensating an offset and adjusting the sensitivity of the pressure transducer to a predetermined level. A reusable cable (160) connected to a pressure monitor (14) is intended for use with a plurality of disposable pressure transducers (12). In one embodiment, a connector (150) of the reusable cable includes a CPU (70), which determines the offset and self-heating errors of the pressure transducer during the first 30 seconds it is energized, stores the corrections in its internal memory and compensates the output signal produced by the pressure transducer for those errors and for variations in ambient temperature. A gain-set resistor (56) is included in a male modular phone plug (202) of a disposable cable that is integrally connected to the pressure transducer, and is used by the compensation circuit to control the signal produced by the pressure transducer, compensating for the characteristic sensitivity of the device. In a second embodiment, the disposable cable includes an offset resistor (250), and the compensation system uses a charge balance modulator 9260) to produce a pulse width modulated signal that is compensated for both the offset and characteristic sensitivity of the pressure transducer.

19 Claims, 6 Drawing Sheets

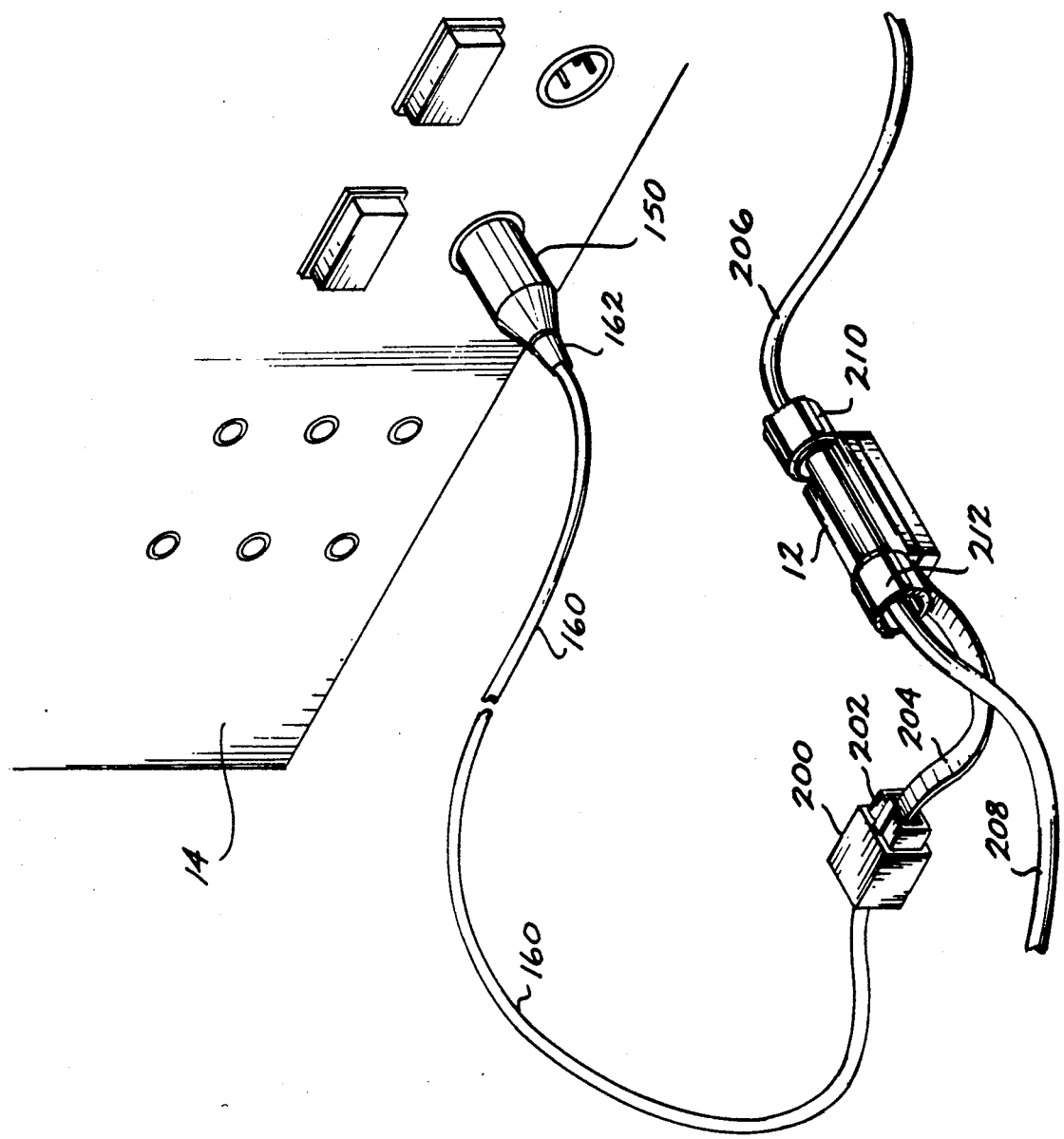

PRESSURE TRANSDUCER COMPENSATION SYSTEM

TECHNICAL FIELD

The present invention generally relates to pressure transducers, and particularly to a system for compensating errors in a pressure transducer.

BACKGROUND OF THE INVENTION

Low-cost, solid-state pressure transducers have greatly improved the medical practitioner's ability to continuously monitor a patient's hemodynamic pressure. In a typical application, a pressure transducer is connected to a patient through an intravascular catheter; its output signal is processed and displayed either digitally in units of pressure, or as a time varying analog trace on a cathode ray tube (CRT) monitor. Once a pressure transducer is connected to monitor a patient's blood pressure, it becomes contaminated and cannot be used with another patient unless sterilized. The medical industry has voiced a clear preference for low-cost pressure transducers that are used with one patient and then discarded. In response, manufacturers have been compelled by competition to further reduce the cost of each new generation of pressure transducer design.

A conventional low-cost pressure transducer typically includes a Wheatstone bridge resistor network deposited on a silicon chip. The resistor network is subject to errors in sensitivity and changes in zero offset caused by temperature effects, which can significantly affect the accuracy of the pressure transducer. Temperature related errors include both those caused by self-heating and errors caused by changes in ambient temperature. Compensation for sensitivity, offset, ambient temperature and self-heating errors have been provided in prior art devices, either integrally on the silicon pressure transducer chip, or on a separate circuit within the pressure transducer housing. An example of the latter type of compensation circuit is disclosed in U.S. Pat. No. 4,576,181.

U.S. Pat. No. 4,557,269, assigned to the same assignee as is the present invention, discloses still another approach to calibrating a disposable pressure transducer. After the pressure transducer is fabricated, it is calibrated to compensate errors in its Wheatstone bridge circuit by trimming a plurality of resistors that are diffused onto a separate semiconductor substrate. Instead of including this semiconductor substrate inside the pressure transducer housing, it is mounted on an external disposable card. The card is plugged into a connector formed on the end of the pressure transducer housing, and stays with the pressure transducer during its use and subsequent disposal. An interface circuit is provided between the pressure transducer and an electromanometry system in which the transducer is used as the pressure sensing element.

While presently available disposable pressure transducers are already relatively inexpensive, there is clearly motivation for reducing their cost even further. The lowest cost, reliable pressure transducer on the market has a significant competitive advantage.

Accordingly, it is an object of the present invention to effect a significant reduction in the cost of disposable pressure transducers without incurring a concomitant decrease in quality. Further, it is an object to reduce the cost of the pressure transducer by including offset, self-heating, and ambient temperature compensation, sensitivity adjustment, and impedance matching in a reusable cable interface that is connected between the disposable pressure transducer and a pressure monitor. These and other objects and advantages of the present invention will be apparent from the attached drawings and the description of the preferred embodiments that follow.

SUMMARY OF THE INVENTION

In accordance with the present invention, a pressure transducer compensation system is provided for use with disposable pressure transducers. The compensation system includes means associated with each disposable pressure transducer for defining the sensitivity of the disposable pressure transducer to pressure. Sensitivity control means are connected to the means for defining the sensitivity and are operative to control the compensation system in response thereto, to effect a predefined sensitivity to pressure.

Means are provided for determining an offset of the disposable pressure transducer. The compensation system also includes means operative to compensate the output signal of the disposable pressure transducer for the offset during use of the transducer in monitoring pressure. Means are provided for determining a self-heating error and a correction for changes in ambient temperature when the pressure transducer is first energized. During its use, means included in the system compensate the output signal for the self-heating error and for changes in ambient temperature.

The pressure transducer compensation system further includes means for matching an output impedance of the compensation system with an input impedance of a pressure monitor. A power supply in the compensation system derives power from an excitation current normally supplied to the disposable pressure transducer by the pressure monitor.

In determining the offset, self-heating error, and ambient temperature correction, initial values for the transducer output signal and a transducer excitation voltage are determined for the disposable pressure transducer when it is first energized, and second such values are determined after it has been energized for a predetermined interval of time. Compensation for the offset, self-heating error, and ambient temperature change is determined as a function of the differences between the initial and second values. Means are included for digitally storing the offset, self-heating error, and temperature correction of the disposable pressure transducer. Alternatively, the means for determining the offset of the disposable pressure transducer may comprise a resistor disposed within a cable integral with the pressure transducer.

Another aspect of the present invention is a method for compensating errors in a pressure transducer. The method includes steps generally corresponding to the functions implemented by the various elements described above.

BRIEF DESCRIPTION OF THE DRAWINGS

FIG. 6 is an isometric view of a pressure transducer used for monitoring blood pressure, as it is connected through the pressure transducer compensation system to a pressure monitor.

DESCRIPTION OF THE PREFERRED EMBODIMENTS

Figure 1:
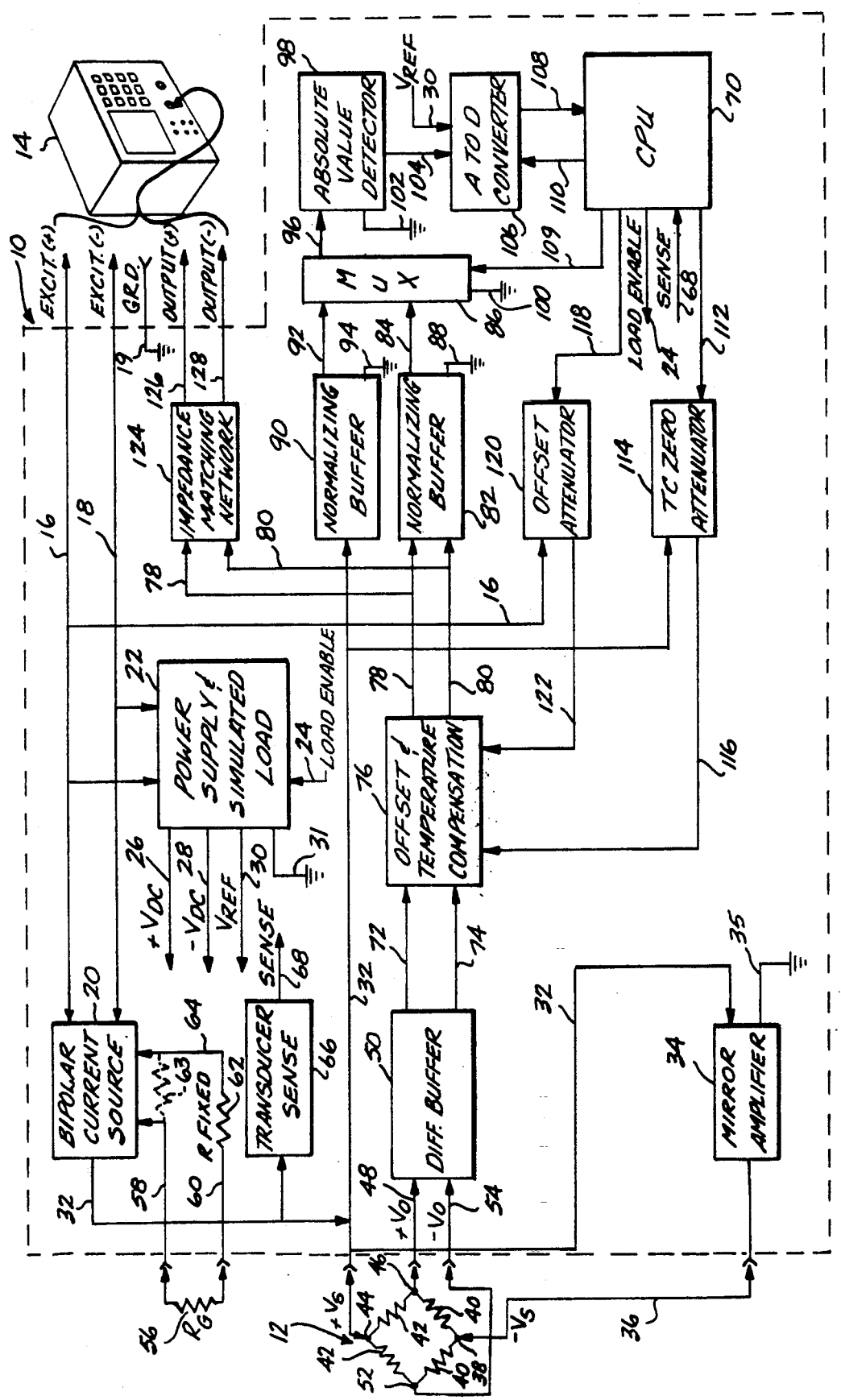
FIG. 1 is a schematic block diagram illustrating components of a first embodiment of the present invention with respect to their use with a pressure monitor.

A pressure transducer intended for use in monitoring the intravascular blood pressure of a patient, as transmitted through fluid in a catheter, is shown in FIG. 6, generally represented by reference numeral 12. Pressure transducer 12 includes two luer fittings 210 and 212, which are connected respectively to catheter lines 206 and 208. Catheter line 206 may, for example, be connected to a bottle or bag of medicinal fluid (not shown), while catheter line 208 intravenously penetrates the patient's body. Pressure transducer 12 responds to the intravenous pressure of the patient, which is transmitted via the medicinal fluid flowing within catheter line 208, and produces an output signal indicative of that pressure.

The output signal produced by pressure transducer 12 is conveyed through a multiconductor cable 204, which is terminated in a generally conventional male modular telephone jack 202. Male modular telephone jack 202 is plugged into an appropriate female modular telephone jack 200, and thus, is connected to a plurality of conductors (not shown) within a reusable cable 160. Reusable cable 160 passes through a strain relief 162 and is terminated within a connector 150 that is plugged into a pressure monitor 14. Pressure transducer 12, multiconductor cable 204 and male modular telephone jack 202 are considered disposable, and are not intended to be sterilized for reuse with another patient. Conversely, reusable cable 160, along with female modular telephone connector 200 and connector 150, is intended for use with a plurality of pressure transducers, each generally similar to pressure transducer 12.

Each pressure transducer used with reusable pressure transducer cable 160 has a characteristic offset and temperature error. The temperature error includes an error due to self-heating and an error due to changes in ambient temperature. Among similar pressure transducers, these values are likely different, due, for example, to variations in temperature coefficients and internal resistance values of the transducers. In addition, the sensitivity of any pressure transducer to pressure may vary from a nominal specified value, in comparison to the sensitivity of other similar pressure transducers. The characteristic errors and sensitivity of each pressure transducer are not compensated within pressure transducer 12, as is typically done. Instead, the pressure transducer compensation system of the present invention compensates each pressure transducer connected to reusable cable 160, so that pressure monitor 14 sees a substantially "perfect" pressure transducer each time a different pressure transducer 12 is connected to monitor pressure in a patient.

Turning now to FIG. 1, a first embodiment of a compensation circuit 10 is shown in the form of a block diagram. Compensation circuit 10 is disposed within connector 150 (shown in FIG. 6); it is connected to pressure transducer 12 (shown on the left side of FIG. 1), and to pressure monitor 14 (as indicated in the upper right of FIG. 1). Pressure monitor 14 produces an excitation voltage that is applied to compensation circuit 10 through leads 16 and 18. These leads provide a signal to a bipolar current source 20 and power to a power supply/simulated load 22. Power supply/simulated load 22 produces three output voltages, including $\pm V_{DC}$, on leads 26 and 28, and a regulated reference voltage, $V_{REF}$, on a lead 30. Ground reference for the compensation circuit is provided on a lead 31. A signal controlling the enablement of a simulated load is input to power supply/simulated load 22 through a lead 24; its function is explained below.

Bipolar current source 20 comprises a voltage-to-current converter that produces an output current on a lead 32. The output current from bipolar current source 20 is proportional to the excitation voltage appearing across leads 16 and 18 and is either a direct current or an alternating current, depending on the nature of the excitation voltage on leads 16 and 18. Lead 32 is connected to the input of a mirror amplifier 34, which is referenced to ground through a lead 35. Mirror amplifier 34 produces an output voltage on a lead 36 that is equal in magnitude, but opposite in polarity to the voltage on lead 32.

Lead 36 connects to a node 38 of pressure transducer 12, while lead 32 connects to a node 44. As shown in FIG. 1, pressure transducer 12 comprises two resistors 40, connected at one end to form node 38 and two resistors 42, which are connected at one end to form node 44. The other ends of resistors 40 and 42 are connected to form nodes 46 and 52, and the four resistors are thus configured as a Wheatstone bridge. Resistors 40 and 42 are deposited on a semiconductor substrate (not shown) having a relatively thin cross section. Deflection of the semiconductor substrate due to pressure changes the relative resistance of these resistors, creating an imbalanced potential between nodes 46 and 52. Accordingly, the voltage developed across nodes 46 and 52 of pressure transducer 12 is a function of the applied pressure. An output signal from pressure transducer 12 appears on leads 48 and 54, which are respectively connected to nodes 46 and 52. Pressure transducer 12 is preferably referenced to atmospheric pressure, and thus its output signal is indicative of "gage pressure".

Since a typical low-cost pressure transducer has a characteristic sensitivity to pressure that may be different than other similar pressure transducers, it usually includes an individually trimmed calibration network that is either disposed on the substrate of the pressure transducer, or separately provided within the transducer housing. The calibration network adds to the cost and complexity of the pressure transducer. However, in the present compensation system, a somewhat simpler approach is used, wherein a single, low cost gain-set resistor 56 is individually selected for use with each pressure transducer 12 after its fabrication. The value of gain-set resistor 56 depends on the measured sensitivity of the pressure transducer, and is selected to compensate for the deviation of the transducer's pressure sensitivity from a nominal specified value.

As shown in FIG. 1, gain-set resistor 56 is connected to bipolar current source 20 by means of leads 58 and 60. Gain-set resistor 56 is preferably disposed within male modular telephone jack 202, and thus is part of disposable multiconductor cable 204. Since multiconductor cable 204 is integral with pressure transducer 12, gain-set resistor 56 is discarded, along with pressure transducer 12, following use of the pressure transducer with one patient. The resistance of gain-set resistor 56 is in series with a fixed resistor 62, which is connected to bipolar current source 20 by a lead 64. Fixed resistor 62 establishes a lower tolerance requirement for the resistance of gain-set resistor 56. Alternatively, as indicated with dashed lines, a fixed resistor 63 may be connected between leads 64 and 58 in place of fixed resistor 62. Gain-set resistor 56 establishes a proportionality constant between the excitation voltage applied to bipolar current source 20 and the current applied to excite pressure transducer 12 through leads 32 and 36 so that each pressure transducer appears to have the same nominal specified sensitivity.

Leads 48 and 54 connect the output signal from the pressure transducer to the input of a differential buffer 50, which isolates pressure transducer 12 from the remainder of compensation circuit 10. The output of differential buffer 50 is conveyed over leads 72 and 74 to the input of an offset and temperature compensation block 76. As used in this description, and with respect to the claims that follow, the term "offset" refers to the deviation of the output signal of pressure transducer 12 from an indicated zero gage pressure when the pressure transducer is exposed to atmospheric pressure, i.e., when the gage pressure should equal zero. Unless compensated, the offset appears as a fixed error in the output signal of pressure transducer 12.

Additional sources of error relate to the self-heating of pressure transducer 12 and variations in its output caused by ambient temperature changes. A temperature coefficient associated with the pressure transducer 12 determines to what extent its output signal is affected by temperature. Current flowing through resistors 40 and 42 causes self-heating, producing an error that depends on the magnitude of the temperature change induced by self-heating and the temperature coefficient. Compensation circuit 10 determines the offset, self-heating error and ambient temperature correction of the pressure transducer, and applies compensating corrections that are added to the output signal within offset and temperature compensation block 76. The manner in which these corrections are determined is described below. A corrected output signal to which the appropriate compensation has been applied is conveyed via leads 78 and 80 to a normalizing buffer 82 and to an impedance matching network 124. The impedance matching network matches the output impedance of offset and temperature compensation block 76 to the input impedance of pressure monitor 14. An output signal from compensation circuit 10 is supplied to pressure monitor 14 through leads 126 and 128.

The excitation current applied to pressure transducer 12 via lead 32 is also input by the lead to a normalizing buffer 90. Normalizing buffer 90, which is referenced to ground by a lead 94, substantially attenuates the excitation current, producing a corresponding output voltage on a lead 92. Lead 92 connects to one of two inputs of a multiplexer 86. In addition, an output signal from a normalizing buffer 82 is connected through a lead 84 to the other input of multiplexer 86. Normalizing buffer 82 is referenced to ground via a lead 88; its function is to amplify the signal output from offset and temperature compensation block 76.

Multiplexer 86 selects either the signal on lead 92 or the signal on lead 84 for input through a lead 96 to an absolute value detector 98. Absolute value detector 98 is connected to ground through a lead 102 and has an output connected through a lead 104 to an A-to-D converter 106. The absolute value detector rectifies and integrates any AC signal applied to it through lead 96 from multiplexer 86, producing a DC output that is input to the A-to-D converter. A-to-D converter 106 is preferably of the charge balance type; it is referenced to the voltage $V_{REF}$ produced by power supply/simulated load 22 and output on lead 30.

A-to-D converter 106 is connected to a central processing unit (CPU) 70 via leads 108 and 110. In the preferred embodiment, CPU 70 includes a four-bit microprocessor, 512 bytes of read only memory (ROM), and 16 bytes of random access memory (RAM). The preferred embodiment of compensation circuit 10 uses a National Semiconductor Corporation, Type COP 411C microcomputer for CPU 70, although equivalent devices may also be used.

In response to a data request signal conveyed from CPU 70 to the A-to-D converter over lead 110, a digital value corresponding to the analog signal input to the A-to-D converter is output on lead 108. Using the digital values provided on lead 108, and in accordance with a predetermined program stored in ROM, CPU 70 determines the offset and temperature compensation to be applied to the output signal from pressure transducer 12. Digital values for the compensation are supplied through leads 118 and 112, respectively, to offset attenuator 120 and temperature coefficient (TC) zero attenuator 114.

CPU 70 determines whether pressure transducer 12 is connected to leads 32 and 36 in response to a sense signal provided over a lead 68 from transducer sense block 66. Lead 32 is also connected to transducer sense block 66, so that excitation current applied to pressure transducer 12 can be detected. When excitation current flows through lead 32, transducer sense block 66 produces a sense signal on lead 68 indicating that a pressure transducer is connected to compensation circuit 10. In response to the sense signal, CPU 70 produces a load enable signal on lead 24 for input to power supply/simulated load 22. When a pressure transducer 12 is disconnected from compensation circuit 10, or if compensation circuit 10 is energized while a pressure transducer is not connected, CPU 70 turns off the load enable signal. In response to the load enable signal, power supply/simulator load 22 connects a simulated load included within it to leads 16 and 18, increasing the load on pressure monitor 14 sufficiently so that internal circuitry in the pressure monitor reacts as if a more conventional pressure transducer were connected. Many pressure monitors include alarms to alert medical personnel should a pressure transducer become disconnected from the monitor. The simulated load provided by power supply/simulated load 22 is necessary since the combined electrical load of pressure transducer 12 and all other components of the compensation circuit is substantially less than that of a conventional pressure transducer. Most pressure monitors respond to the relatively minimal load thus imposed as if pressure transducer 12 were not even connected, unless the additional simulated load is provided by power supply/simulated load 22.

Figure 5:
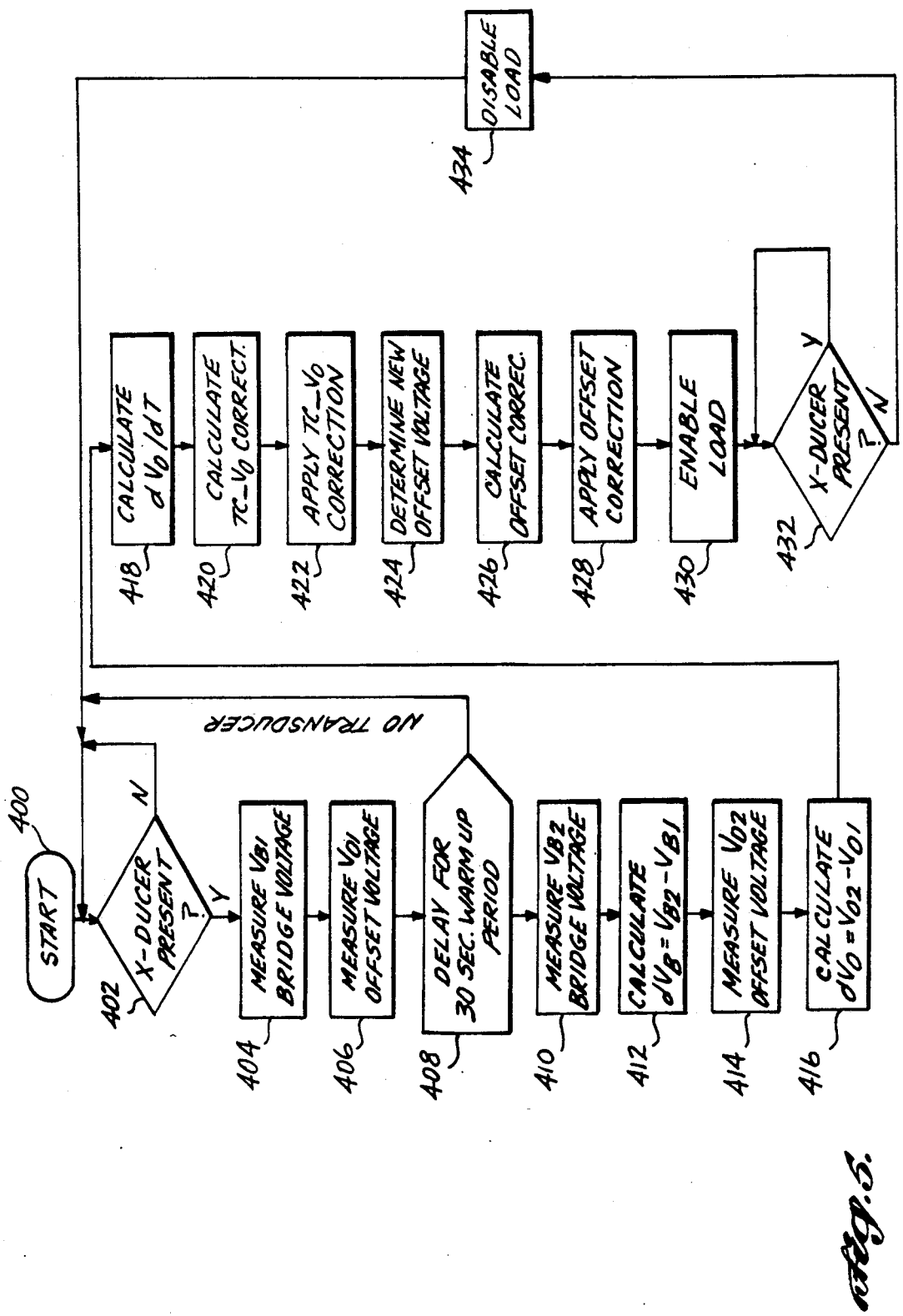
FIG. 5 is a flow chart showing the logic implemented by a microprocessor in the first preferred embodiment of the pressure transducer compensation system.

Turning now to FIG. 5, logic implemented by CPU 70 in determining and applying compensation for the offset and temperature error of pressure transducer 12 is shown in a flow chart. The flow chart begins at block 400, and proceeds to a decision block 402, wherein the transducer sense signal on lead 68 is checked to determine if pressure transducer 12 is connected to compensation circuit 10. This check is repeated until the transducer sense signal indicates that pressure transducer 12 is connected to compensation circuit 10, at which point the logic advances to block 404. In block 404, the initial excitation voltage (bridge voltage), $V_{B1}$, on lead 32 is measured. CPU 70 produces an appropriate selection signal on a lead 109, causing multiplexer 86 to select the output signal from normalizing buffer 90 for input to absolute value detector 98. The term "measured", as used herein, corresponds to selection of the required voltage by multiplexer 86, and conversion of the absolute value of the signal to a digital equivalent by A-to-D converter 106. The value $V_{B1}$ is stored in RAM by CPU 70 for later use.

In block 406, CPU 70 causes an initial output signal from the pressure transducer to be measured (i.e., the signal on leads 78 and 80), producing the value $V_{01}$. At this point, it is important that the pressure transducer not yet be connected to monitor the intravascular pressure of a patient; instead, it must be exposed to atmospheric pressure, i.e., to a zero gage pressure. To measure voltage $V_{01}$, CPU 70 provides the appropriate selection signal on lead 109, causing multiplexer 86 to select the output from normalizing buffer 82 for input to the absolute value detector and the A-to-D converter. Since the output signal of the pressure tranducer should indicate zero gage pressure at this time, the voltage $V_{01}$ represents an initial offset of pressure transducer 12.

After measuring both $V_{B1}$ and $V_{01}$, CPU 70 waits for a predetermined time period to permit self-heating of pressure transducer 12, caused by the flow of current through resistors 40 and 42 in the Wheatstone bridge, to reach equilibrium. In the preferred embodiment, the time delay is set at approximately 30 seconds. If during the delay period, the pressure transducer is disconnected from the compensation circuit, the logic of the flow chart proceeds back to block 402. Following the time delay for self-heating in block 410, CPU 70 measures a second excitation voltage, $V_{B2}$, on lead 32; and in block 412, CPU 70 calculates $dV_B$, which is equal to the difference between $V_{B2}$ and $V_{B1}$. Immediately thereafter, CPU 70 again measures the output signal on lead 84 to obtain a value for the voltage $V_{02}$, which represents a second offset voltage. In block 416, CPU 70 calculates $dV_0$, which is equal to the difference between $V_{02}$ and $V_{01}$.

Block 418 of the flow chart indicates that CPU 70 calculates a value $dV_0/dT$, where $dT$ is equal to $dV_B/(TC_R \cdot V_{B1})$, and where $TC_R$ is the temperature coefficient of resistance for the pressure transducer (equal to about 0.0022 for pressure transducers of the type used with the preferred embodiment). A correction for temperature error, $TC - V_0$, is determined in block 420, which is equal to $-(dV_0/dT)/TC_R$. This correction for temperature error comprises a correction for both self-heating error and changes in ambient temperature.

Having determined the correction for temperature error, CPU 70 produces a corresponding digital signal on lead 112, which is input to TC zero attenuator 114. TC zero attenuator 114 converts the digital signal to an analog signal that is input to offset and temperature compensation block 76 over lead 116. This temperature error compensation increases the magnitude of the offset. After supplying compensation for the temperature error in block 422, CPU 70 measures a new output signal offset in block 424 by selecting normalizing buffer 82, so that the output signal from pressure transducer 12 is digitized. An offset compensation is calculated in block 426, equal in magnitude but opposite in sign to the new output signal, and when applied, produces a net output signal equal to zero. In applying the correction in block 428, the offset compensation is provided as a digital signal through lead 118 to offset attenuator 120, and is thereby converted to an analog value, which is input over lead 122 to offset and temperature compensation block 76. By initially correcting for the effects of self-heating and ambient temperature change before determining and applying offset compensation, the correction for offset is made more accurate. In addition, it should be noted that TC zero attenuator 114 is referenced to the excitation voltage on lead 32, so that any variation in the voltage on lead 32 is automatically taken into consideration in developing the analog temperature compensation applied via lead 116.

In block 430, CPU 70 produces the load enable signal, causing power supply/simulated load 24 to apply the simulated load to leads 16 and 18. The load enable signal is maintained so long as a continually repeating check in block 432 determines that pressure transducer 12 is connected to compensation circuit 10. If the pressure transducer is disconnected, CPU 70 deenergizes the load enable signal as indicated in block 434, causing the logic to return to block 402.

Compensation circuit 10 repeats the determination of offset and temperature compensation each time that the compensation circuit is reenergized, or each time that a pressure transducer is initially connected to the compensation circuit. Compensation of the output signals from each pressure transducer 12 is continually provided while that transducer is in use; however, should a new pressure transducer be connected, the values applied for compensation are redetermined so that each pressure transducer has an appropriate offset and temperature compensation applied to correct its characteristic errors. In addition, since each pressure transducer includes its own gain-set resistor 56, selected to compensate for the sensitivity of that particular pressure transducer, compensation circuit 10 automatically adjusts the current applied to the pressure transducer, so that pressure monitor 14 is supplied with a pressure transducer output signal of the nominal specified pressure sensitivity.

Figure 2:
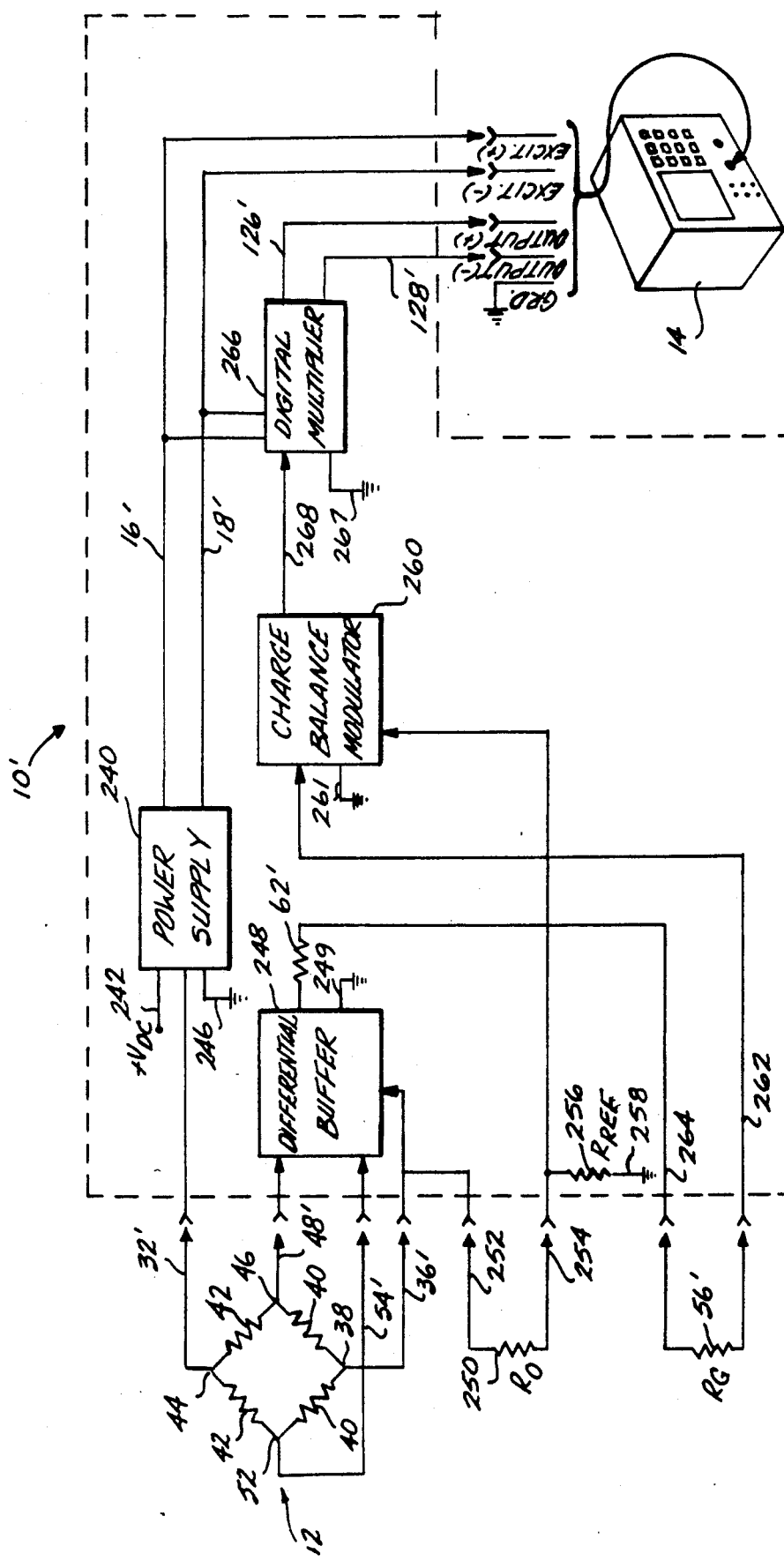
FIG. 2 is a schematic block diagram illustrating a second preferred embodiment of the pressure transducer compensation system.

There are certain medical pressure measurement applications wherein failure of a user to initially apply ambient pressure to pressure transducer 12, to enable the compensation system to properly determine an offset for zero gage pressure, can cause serious errors. Accordingly, a second embodiment of the present invention shown in a block diagram in FIG. 2 was developed that eliminates this requirement. The second embodiment includes a compensation circuit generally denoted at reference number 10'. Excitation power from pressure monitor 14 is provided through leads 16' and 18' to a power supply 240, having an output lead 242 on which an appropriate voltage, $+V_{DC}$, is provided to each of the power consuming components within compensation circuit 10'; in addition, power supply 240 is connected to a ground lead 246. Power supply 240 provides excitation voltage through a lead 32' to node 44 of pressure transducer 12. Node 38 of the transducer is connected to a differential buffer 248 by a lead 36', and the output signal of the pressure transducer, which appears across nodes 46 and 52, is connected through leads 48' and 54' to the differential buffer. Differential buffer 248 is referenced to ground through a lead 249. The function of the differential buffer is to isolate the remainder of compensation circuit 10' from the pressure transducer and to amplify the pressure transducer output signal.

The second preferred embodiment of the compensation system includes both a gain-set resistor 56' and an offset resistor 250, both disposed within male modular telephone connector 202 (shown in FIG. 6). Resistance values for the gain-set resistor and offset resistor are both determined after fabrication of pressure transducer 12 as appropriate to compensate for its individual pressure sensitivity and zero offset.

In the second preferred embodiment, no provision is made for determining or applying a correction for self-heating of the pressure transducer or for ambient temperature changes, at least within compensation circuit 10'. However, it will be understood by those of ordinary skill in the art that self-heating and ambient temperature compensation may be provided within pressure transducer 12 by use of appropriate trim components (not shown). Alternatively, the self-heating and ambient temperature change error may be ignored if the magnitude of its effect is minimized in the manufacture of the pressure transducer.

Offset resistor 250 is connected through a lead 252 to lead 36', and thus to differential buffer 248. In addition, it is connected through a lead 254 to one side of a resistor 256, and to a charge balance modulator 260, which is referenced to ground through a lead 261. The other side of resistor 256 is grounded through a lead 258. Offset resistor 250 controls the level of a bias voltage applied to the output signal from pressure transducer 12, and is connected in series with resistor 256, with respect to current flow to ground.

From differential buffer 248, the output signal passes through a fixed gain resistor 62' into a lead 264, through gain-set resistor 56', and through a lead 262 to the input of charge balance modulator 260. Gain-set resistor 56' and fixed resistor 62' together establish current flow into the charge balance modulator, and thereby fix the effective pressure sensitivity of pressure transducer 12 at the nominal specified value with respect to the signal input to pressure monitor 14.

Charge balance modulator 260 produces a series of output pulses that vary in width in proportion to the output signal from pressure transducer 12. The output pulses are input over a lead 268 to a digital multiplier circuit 266, which is referenced to ground by a lead 267. Digital multiplier 266 supplies pulse width modulated current provided from the excitation supply on leads 16' and 18' to pressure monitor 14 over leads 126' and 128'. The pressure monitor integrates the output pulses and displays a pressure reading indicative of the pressure sensed by pressure transducer 12.

Figure 3:
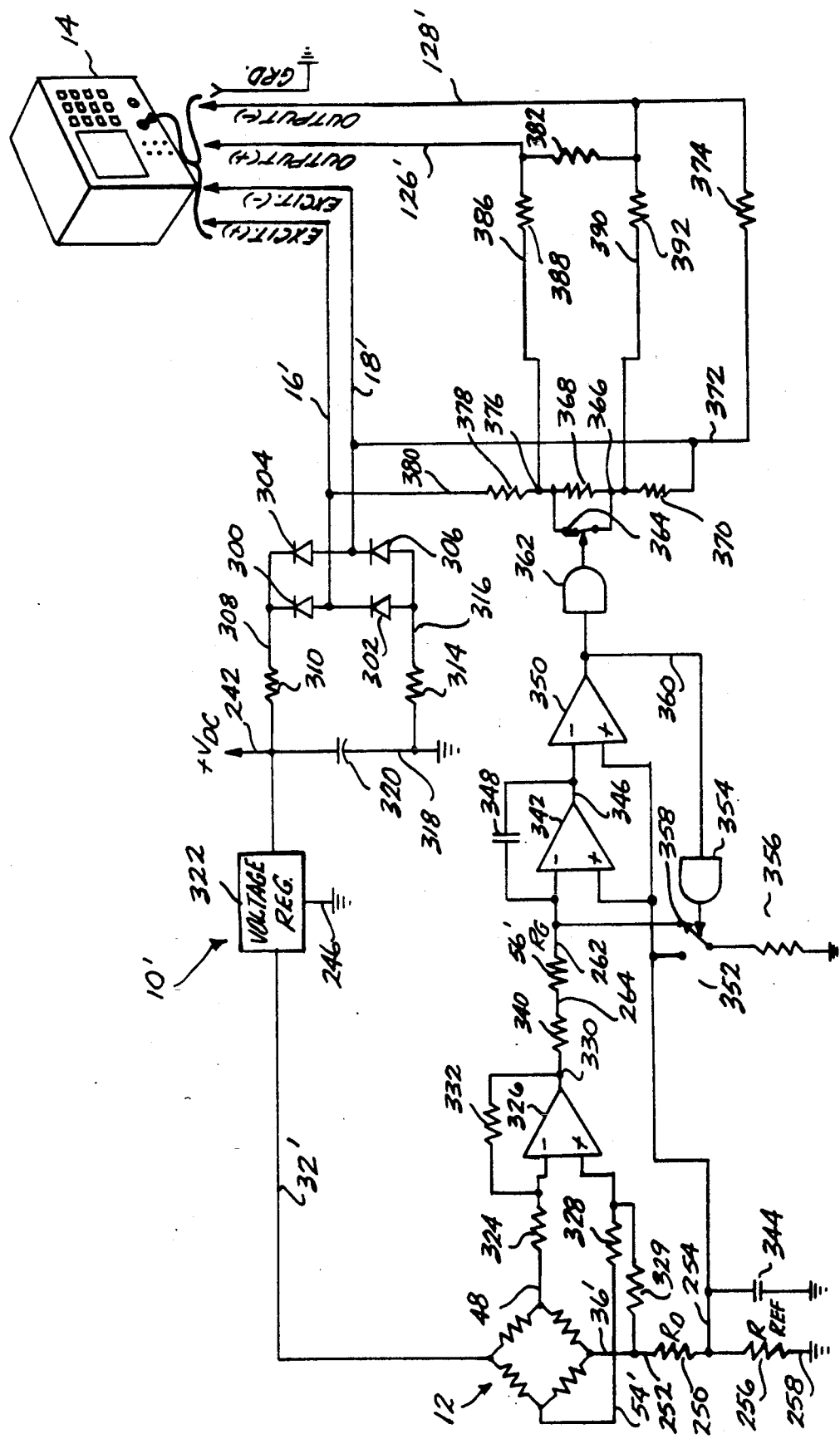
FIG. 3 is a detailed schematic circuit of the second preferred embodiment of the pressure transducer compensation system.

Details of compensation circuit 10' are shown in FIG. 3. The power supply of compensation circuit 10' includes a full wave rectifier, comprising diodes 300, 302, 304 and 306. Diodes 300 and 304 convey positive current respectively from leads 16' and 18' to a lead 308, which is connected to a resistor 310; diodes 302 and 306 convey negative current to a lead 316, which is connected to ground through a resistor 314 and a lead 318. A capacitor 320 filters the full wave rectified voltage between resistors 310 and 314 and is connected to ground through a lead 318. The rectified and filtered supply voltage is input to an integrated circuit voltage regulator 322, the output of which is connected to lead 32'.

Lead 36' from the pressure transducer is connected to ground through series connected resistors 250 and 256, as previously explained. The resistance of the offset resistor 250 used with pressure transducer 12 is selected to compensate for the offset in the output signal of the pressure transducer when zero gage pressure is applied. The voltage developed across resistor 250, with respect to a reference voltage developed across resistor 256, is applied to the noninverting input of an op amp 326, and is thereby summed with the voltage from the pressure transducer, which is supplied through a resistor 328 from lead 54'. The inverting input of op amp 326 is connected to the output signal of the pressure transducer, through an input resistor 324 and lead 48'. A feedback resistor 332 connects the output of op amp 326 to its inverting input. The gain of op amp 326 is equal to the ratio of feedback resistor 332 and input resistor 324, offset by the voltage developed across offset resistor 250.

A resistor 340 is connected to the output of op amp 326 in series with gain-set resistor 56'. Resistors 340 and 56' establish current flow into charge balance modulator 260. The charge balance modulator comprises integrator op amp 342 and comparator 350. Lead 262, which is connected to gain-set resistor 56', conveys charging current into the inverting input of integrating op amp 342. Lead 262 is also connected to a terminal 358 of an electronic switch 354, the purpose of which is explained below. The output of integrating op amp 342 is connected through a lead 346 to a feedback capacitor 348, while its noninverting input is connected to lead 254 and to a terminal 352 of electronic switch 354. The "toggle" of electronic switch 354 is connected through a resistor 356 to ground.

Lead 346 also connects the output of integrating op amp 342 to the inverting input of comparator 350; the noninverting input of comparator 350 is connected to lead 254, and thus to the reference voltage developed across ($R_{REF}$) resistor 256. The output of comparator 350 is connected through lead 360 to the input of electronic switch 354, and controls the terminal to which the switch toggle is connected. In FIG. 3, the toggle of electronic switch 354 is disposed to provide continuity between terminal 358 and ground through resistor 356. In this position, electronic switch 354 is operative to discharge capacitor 348. However, when the input voltage to electronic switch 354 (on lead 360) is deenergized, the toggle actuates, connecting resistor 356 to terminal 352. When connected to terminal 352, an internal capacitance of the electronic switch 354 is held at the reference voltage on lead 254, so that the internal capacitance of the switch does not bleed current from lead 262 when the toggle is reconnected to terminal 358.

Integrating op amp 342 produces an output current that charges capacitor 348 as the op amp attempts to maintain its inverting and noninverting inputs at the same potential. The potential on output lead 346 of integrating op amp 342 ramps downwardly as capacitor 348 charges, and when the potential on lead 346 exceeds the reference voltage on lead 254, comparator 350 saturates, i.e., its output voltage changes from approximately zero to the supply voltage, $+V_{DC}$. In response to the $+V_{DC}$ potential on lead 360, electronic switch 354 connects resistor 356 to terminal 358, discharging capacitor 348. As capacitor 348 discharges, the voltage applied to the inverting input of comparator 350 rises above the reference voltage, forcing the output of comparator 350 back to zero volts. Electronic switch 354 then toggles resistor 356 to terminal 352, permitting capacitor 348 to recharge.

The repetitive charge/discharge cycling of capacitor 348 continues so long as the voltage on lead 330 is greater than the reference voltage on lead 254. The potential appearing on lead 360 thus comprises a series of pulses at a frequency that changes slightly as the output signal from pressure transducer 12 changes. More importantly, the ratio of on-time to off-time of the pulses that appear on lead 360 is directly proportional to the amplitude of the output signal from pressure transducer 12 at lead 330. In a preferred embodiment, the nominal frequency of the pulse signal on lead 360 is approximately 150 kilohertz at a 50% pulse duty cycle. The range of pressure transducer 12 in the preferred embodiment is from −50 millimeters of mercury to 300 millimeters of mercury, corresponding to a duty cycle range from 10% to about 90%, i.e., a pulse width modulated signal in which the ratio of on-time to off-time of the pulses varies from about 10% to about 90%.

The pulse width modulated signal on lead 360 is also applied to the input of an electronic switch 362. Electronic switch 362 is connected to selectively short a resistor 368, which is disposed between a lead 366 and a lead 376, during the off time between successive pulses on lead 360. Lead 376 is connected to a terminal 364 of the electronic switch, and is connected through a resistor 378 and a lead 380 to the excitation voltage on lead 16'. Lead 366 is connected through a resistor 370 and a lead 372 to the excitation voltage on lead 18'. Resistors 378, 368, and 370 are thus connected in series between the potential on lead 16' and 18', so that a potential difference exists between leads 366 and 376 across resistor 368. However, when electronic switch 362 shorts resistor 368, that potential difference drops to zero. Accordingly, electronic switch 362 and resistors 378, 368 and 370 comprise a digital multiplier having an output voltage that varies between zero and some fraction of the voltage on leads 16' and 18'. The word "digital multiplier" is used to describe this portion of compensation circuit 10', since the voltage across resistor 368 changes between zero and a value arbitrarily representing a logic level 1, similar to the logic signals in a typical digital device.

Lead 376 is connected through a lead 386 and a resistor 388 to lead 126', while lead 366 is connected through a lead 390 and a resistor 392 to lead 128'. Lead 372 also connects to a resistor 374, the other side of which is connected to lead 128'. Resistor 374 provides a bias potential to accommodate the −50 to zero millimeters of mercury low end range of the pressure transducer. A resistor 382 connects between leads 126' and 128' and is selected to match the input impedance of pressure monitor 14; its resistance is adjusted to compensate for the effect of the impedance of the other resistors disposed upstream of resistor 382.

The average electrical energy supplied to pressure monitor 14 over leads 126' and 128' in the form of a series of pulses is directly proportional to the pressure applied to pressure transducer 12, compensated for its characteristic sensitivity and offset. Pressure monitor 14 integrates the pulses input to it, and displays a corresponding pressure level, either as an analog trace on a CRT or in a digital format.

Figure 4:
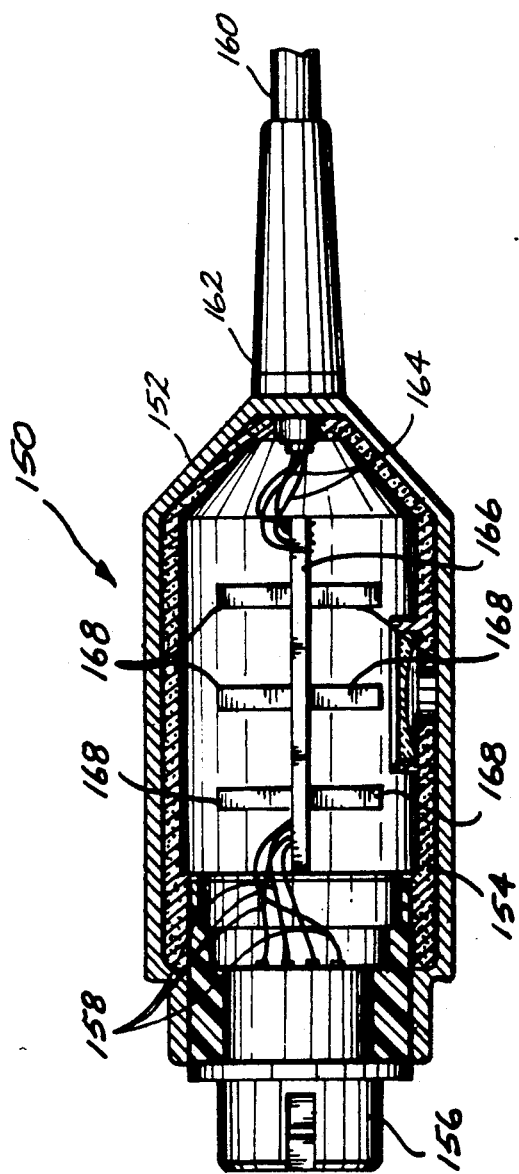
FIG. 4 is a cutaway view of a connector in which is disposed a pressure transducer compensation circuit.

Compensation circuits 10 and 10' are implemented using chip-on-board type printed circuit dies, which enable a relatively large number of components to be formed on a relatively small printed circuit (PC) board 166. PC board 166 is mounted within connector 150, as shown in FIG. 4. No attempt is made in this figure to show the actual components mounted on the PC board; however, it should be understood that they are applied to the surface of the board using conventional techniques. PC board 166 is held in place in slots formed between a plurality of ribs 168 molded into each side of the internal circumference of an inner shell 154 of the connector. Components mounted on PC board 166 are connected to reusable cable 160 through leads 164, and through leads 158 to a multi-prong female plug connector 156.

While the present invention has been disclosed with respect to its preferred embodiments, it should be understood that the scope of the invention is not in any way intended to be limited to the details of the preferred embodiments, but instead should be determined entirely by reference to the claims that follow.

The embodiments of the invention in which an exclusive property or privilege is claimed are defined as follows:

1. A pressure transducer compensation system to compensate for variances in both a characteristic pressure sensitivity and in a zero pressure offset in a pressure transducer, comprising:
   (a) an electrical cable including a plurality of leads that conduct electrical signals to and from the pressure transducer, said electrical signals including an output signal produced by the pressure transducer;
   (b) a gain resistor, disposed in the electrical cable, said gain resistor having a resistance selected to compensate the output signal for the characteristic pressure sensitivity of the pressure transducer; and
   (c) compensation means, electrically connected to the leads of the electrical cable and to the gain resistor, for:
   (i) compensating the electrical signals as a function of the gain resistor, to achieve a predetermined characteristic pressure sensitivity;
   (ii) defining a zero pressure offset compensation for the pressure transducer; and
   (iii) applying the zero pressure offset compensation to the output signal produced by the pressure transducer to compensate the output signal for the zero pressure offset during use of the pressure transducer.

2. The pressure transducer compensation system of claim 1, wherein the compensation means also initially determine a characteristic self-heating error of the pressure transducer and a correction for changes in ambient temperature for the pressure transducer and compensate the output signal produced by the pressure transducer for the self-heating error and the ambient temperature changes.

3. The pressure transducer compensation system of claim 2, further comprising means for supplying an excitation voltage to the pressure transducer, and wherein the compensation means determine the characteristic zero pressure offset and the self-heating error by:
   (a) determining initial values for the output signal and the excitation voltage, while the pressure transducer is at ambient atmospheric pressure, when the pressure transducer is first energized;

(b) at a predetermined interval of time thereafter, determining second values of the output signal and the transducer excitation voltage for the pressure transducer at ambient atmospheric pressure; and (c) determining differences between the initial and the second values of the output signal and the excitation voltage, respectively, the compensation means determining the characteristic zero pressure offset and the self-heating error as a function of these differences.

4. The pressure transducer compensation system of claim 1, wherein the compensation means comprise an offset resistor, disposed in the electrical cable, said offset resistor having a resistance selected to correct for the zero pressure offset in the output signal from the pressure transducer.

5. The pressure transducer compensation system of claim 4, wherein the electrical cable has an end and includes a connector on the end, and wherein the gain resistor and the offset resistor are disposed in the connector.

6. The pressure transducer compensation system of claim 5, wherein the compensation means produce a compensated output signal approximating a predefined pressure transducer, by compensating for variances in the output signal of said pressure transducer to which the compensation means are electrically connected.

7. The pressure transducer compensation system of claim 1, wherein the compensation means include means for matching an output impedance of the compensation means to an input impedance of a pressure monitor.

8. The pressure transducer compensation system of claim 1, wherein the gain resistor has a resistance selected for use in compensating said pressure transducer.

9. The pressure transducer compensation system of claim 1, wherein the compensation means include a power supply.

10. The pressure transducer compensation system of claim 1, wherein the compensation means vary at least one of the electrical signals as a function of the resistance of the gain resistor.

11. The pressure transducer compensation system of claim 1, wherein the compensation means comprise a microprocessor.

12. A reusable pressure transducer compensation system for use with a disposable pressure transducer having a characteristic pressure sensitivity and producing an output signal having a characteristic zero pressure offset, comprising:

(a) means for defining the characteristic pressure sensitivity of the disposable pressure transducer;

(b) sensitivity control means connected to the means for defining the characteristic pressure sensitivity and in response thereto, modifying the output signal to effect a predefined sensitivity to pressure, thereby producing a modified signal;

(c) means for defining the characteristic zero pressure offset of the disposable pressure transducer; and (d) means for compensating the modified signal for an error due to the characteristic zero pressure offset, producing a compensated signal, free of undesired variances due to the characteristic pressure sensitivity and the characteristic zero pressure offset of that pressure transducer.

13. The pressure transducer compensation system of claim 12, further comprising means for determining a self-heating error and a correction for changes in ambient temperature for the disposable pressure transducer when it is first energized, and means for compensating the modified signal for the self-heating error and correcting the modified signal for changes in ambient temperature in producing the compensated signal.

14. The pressure transducer compensation system of claim 13, wherein the means for compensating comprise a microprocessor that determines the characteristic zero pressure offset and means for applying said characteristic zero pressure offset to the modified signal to produce the compensated signal.

15. The pressure transducer compensation system of claim 13, further comprising means for digitally storing the characteristic zero pressure offset, the self-heating error, and the correction for ambient temperature changes of the disposable pressure transducer for use by the means for compensating in producing the compensated signal.

16. The pressure transducer compensation system of claim 12, further comprising a cable through which the output signal is conveyed, wherein the means for determining the characteristic zero pressure offset comprise a resistor disposed within the cable.

17. The pressure transducer compensation system of claim 12, further comprising a cable through which the output signal is conveyed, wherein the means for defining the characteristic pressure sensitivity comprise a resistor disposed within the cable.

18. The pressure transducer compensation system of claim 12, further comprising impedance matching means for matching an output impedance of the compensation system with an input impedance of a pressure monitor.

19. The pressure transducer compensation system of claim 12, further comprising a power supply that supplies a regulated voltage to the disposable pressure transducer.

* * * * *